US006911100B1

(12) United States Patent
Gibbs et al.

(10) Patent No.: US 6,911,100 B1
(45) Date of Patent: Jun. 28, 2005

(54) METHOD FOR CONTROLLING RESIDUAL STRESS IN PROSTHETICS

(75) Inventors: Phillip Martin Gibbs, Winona Lake, IN (US); Dave Wayne Schroeder, Winona Lake, IN (US)

(73) Assignee: Biomet, Inc., Warsaw, IN (US)

( * ) Notice: Subject to any disclaimer, the term of this patent is extended or adjusted under 35 U.S.C. 154(b) by 139 days.

(21) Appl. No.: 10/231,944

(22) Filed: Aug. 30, 2002

(51) Int. Cl.[7] ............................... A61F 2/30; A61F 2/36
(52) U.S. Cl. .................... 148/668; 148/670; 29/407.05; 623/20.35; 623/20.36; 623/23.11
(58) Field of Search ................................. 148/565, 668, 148/670; 29/407.05; 72/53; 623/20.35, 20.36, 22.3, 23.11

(56) References Cited

U.S. PATENT DOCUMENTS

| | | | |
|---|---|---|---|
| 3,117,041 A | 1/1964 | Koistinen | |
| 4,034,585 A | 7/1977 | Straub | |
| 4,191,599 A | 3/1980 | Stickels et al. | |
| 4,659,241 A | 4/1987 | Bamberger et al. | |
| 4,687,487 A | 8/1987 | Hintermann | |
| 5,057,108 A | 10/1991 | Shetty et al. | |
| 5,251,468 A | 10/1993 | Lin et al. | |
| 5,308,412 A | 5/1994 | Shetty et al. | |
| 5,326,376 A | 7/1994 | Warner et al. | |
| 5,372,660 A | 12/1994 | Davidson | |
| 5,415,704 A | 5/1995 | Davidson | |
| 5,443,663 A | 8/1995 | Meletis | |
| 5,490,195 A | 2/1996 | Berkley | |
| 5,498,302 A | 3/1996 | Davidson | |
| 5,611,250 A | 3/1997 | Narai et al. | |
| 5,625,664 A | 4/1997 | Berkley | |
| 5,704,239 A | 1/1998 | Beals et al. | |
| 5,841,033 A | 11/1998 | Burris et al. | |
| 6,012,316 A | 1/2000 | Lange et al. | |
| 6,025,536 A | 2/2000 | Bender et al. | |
| 6,059,830 A | 5/2000 | Lippincott, III et al. | |
| 6,067,701 A | 5/2000 | Vandewalle | |
| 6,226,597 B1 | 5/2001 | Eastman et al. | |
| 6,231,956 B1 | 5/2001 | Brenner et al. | |
| 6,319,286 B1 * | 11/2001 | Fernandez et al. | 623/23.18 |
| 2004/0016651 A1 * | 1/2004 | Windler | 205/661 |

FOREIGN PATENT DOCUMENTS

| | | |
|---|---|---|
| CA | 2282035 | 3/2000 |
| DE | 4414999 A1 * | 11/1995 |

OTHER PUBLICATIONS

The American Heritage Dictionary of the English Language, 1976, p. 433, definition of "engineering".*

Webster's Ninth New Collegiate Dictionary, 1985, p. 412, definition of "engineering".*

* cited by examiner

Primary Examiner—George Wyszomierski
(74) Attorney, Agent, or Firm—Harness, Dickey & Pierce, P.L.C.

(57) ABSTRACT

A method for producing predetermined internal stresses in a prosthetic device for implantation. The method includes first determining internal stresses which are preferred in prosthetics to instill a particular strength and longevity to the prosthetic. In particular, internal stresses may be used to increase the strength of smaller prosthetic devices. Additionally, once the preferred internal stresses are determined, the internal stresses can be cold worked into subsequent prosthetic devices to instill the same characteristics. Once parts are manufactured, internal stresses can be measured to validate manufacturing process and serve as verification for quality control purposes. Producing prosthetic devices, including predetermined internal stresses through work hardening the prosthetic devices, is described.

36 Claims, 3 Drawing Sheets

METHOD FOR CONTROLLING RESIDUAL STRESS IN PROSTHETICS

TECHNICAL FIELD

The present invention relates to producing prosthetics, and particularly relates to a method of producing predetermined residual stresses in prosthetics.

BACKGROUND

It is generally known in the art to use prosthetic devices to replace portions of the human anatomy that have been damaged due to injury or age. Often these prosthetic devices are formed of materials that are inherently strong yet easily formable. Many modular prosthetic devices are formed of at least metal stem portions that are inserted into long bones to provide a base for an external portion that extends from the boney portion. A taper or neck often interconnects the portion that extends from the bone, such as a head of a humerus or a femur, and the stem that is inserted in the bone. A taper may also be used to interconnect modular positions that are disposed within the bone after implantation. It is also known to provide bearing surfaces that must interact with one another while not wearing quickly or producing much wear debris.

The taper or neck that interconnects the two portions of the prosthesis, sometimes referred to as a Morse taper, must be strong enough to withstand cyclic loads that will be seen in a wide variety of anatomies, patient activity levels, and compromised boney constructs. The neck must also allow a range of movement that closely simulates the natural human anatomy. Other types of prosthetic devices are also modular and are formed from multiple interconnecting components. These components may also be interconnected by way of a Morse taper.

While materials generally used in these devices are inherently strong and have high tensile strengths, they require a particular thickness or mass to provide enough support for the portion of the anatomy that is being replaced. Due to this, the Morse taper is often larger and does not provide a full or natural range of motion. If the taper is for internal bone connection, a strong enough connection may produce a taper that is too big to fit into smaller bones. Due to this, it is desirable to produce prosthetic devices that include neck or interconnection portions that are small enough to fit into smaller bones and allow a full range of motion while being strong enough to support the stresses which the prosthetic will encounter.

One solution has been to provide new metal alloys that are particularly strong. These metal alloys may be formed into a myriad of shapes while still providing much of the support necessary for the prosthetic device. These new metal alloys, however, are still required to have large enough interconnection portions to provide the necessary strength to the materials.

Other known methods include the cold working or work hardening of prosthetics, such as that disclosed in the commonly assigned U.S. Pat. No. 6,067,701 entitled "Method for Forming a Work Hardened Modular Component Connector", which is hereby incorporated by preference. These methods, however, include a certain amount of uncertainty introduced into the prosthetic device. Therefore, excessive or unnecessary work hardening may be performed or the prosthetic may not be work hardened enough, requiring an earlier replacement than necessary. In addition, other precautions, such as larger prosthetics, may unnecessarily be used to ensure proper strength.

Cold working induces residual stresses within the component and may also produce the required or different residual stresses within the component. Particular residual stresses can be either compressive or tensile depending upon their nature. Compressive residual stresses are particularly desired. In particular, compressive residual stresses inhibit or stop cracks which may form in the prosthetic device. Furthermore, compressive stresses inhibit the initiation of a crack within the area which is loaded by external forces.

Compressive stress, especially near the surface of the component, also provides additional benefits. In particular compressive stress near the surface can decrease fatigue and stress corrosion failures. In particular, these fatigue and stress corrosion failures originate at the surface and the compressive stress help inhibit such failures. In addition, the compressive residual stresses increase resistance to other undesired events such as fatigue failures, corrosion failure, stress corrosion cracking, hydrogen assisted cracking, fretting, galling, and corrosion caused by cavitation. Additionally, work hardening, which produces the compressive stresses, increases intergranular corrosion resistance, surface texturing, and closing of surface porosity.

Although compressive stresses, or other particular residual stresses, provide these many benefits, it is more beneficial to precisely create the desired residual stresses within the prosthetic device. Although exploratory cold working a component may produce the desired residual stresses, predetermining and work hardening components to produce predetermined residual stresses is preferable. Therefore, it is desired to provide a known process to produce within the prosthetic device, known and predetermined residual stresses that will provide compressive and tensile stresses, that are desired in a component.

Thus, it is desirable to have a method of producing prosthetic devices that leaves no uncertainty to the strength being introduced into the prosthetic device. This would allow for more efficient manufacturing and an increase in prosthetic strength that survive the testing phase. That is, it is desirable to produce a prosthetic device that needs not to be tested as often while still assuring that the prosthetic device will be able to handle the loads after being implanted.

SUMMARY OF THE DISCLOSURE

A method for producing predetermined internal stresses in a prosthetic device for implantation. The method includes first determining internal stresses which are preferred in prosthetics to instill a particular strength and longevity to the prosthetic. In particular, internal stresses may be used to increase the strength of smaller prosthetic devices. Additionally, once the preferred internal stresses are determined, the internal stresses can be cold worked into subsequent prosthetic devices to instill the same characteristics. Producing prosthetic devices, including predetermined internal stresses through work hardening the prosthetic devices, is described.

A first embodiment of the present invention is a method of forming a prosthetic device by determining a use for the prosthetic device. Then determining loads the prosthetic device will encounter in the determined use. Also an internal stress of the prosthetic device which will withstand the loads is determined. The prosthetic device is then formed to include the internal stress.

A second embodiment of the present invention provides a method for producing a prosthetic device for implantation into a body including determining an application for the prosthetic device. The prosthetic device is then formed for the application. Loads incident the prosthetic device, when applied to the determined application, are also determined. A particular internal stress is found so that the prosthetic device, when in the application, may withstand the determined loads. The prosthetic device is then produced with the particular internal stress.

A third embodiment of the present invention is a method of producing a prosthetic for implantation including a particular internal stress, the method including determining a use for a prosthetic member. The prosthetic member is formed and includes a body and a connector. Loads are determined which the connector will encounter after implantation. Particular internal stresses are determined which are generally necessary to withstand the determined loads. Then, cold working the connector produces the particular internal stresses in the connector.

A fourth embodiment of the present invention is a method of producing a prosthetic for implantation having a predetermined particular internal stress. The use for a finished prosthetic member is determined. Then a blank prosthetic member comprising a femoral male taper is formed for the determined use. Particular residual internal compressive stresses between a range of about 40 thousand pounds per square inch (ksi) to about 120 ksi to be formed in a region between an exterior surface of said femoral male taper and about 3.0 mm below the exterior surface are predetermined to be formed in the blank prosthetic. The blank prosthetic member is work hardened to produce the predetermined internal stresses at the predetermined depths in the blank prosthetic to form the finished prosthetic member.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE EMBODIMENTS

The following description of the preferred embodiment(s) is merely exemplary in nature and is in no way intended to limit the invention, its application, or uses. Although the following description relates primarily to a Morse taper, it will be understood that the disclosed invention may relate to any portion of any prosthetic device requiring a certain internal residual stress, including other connection portions, bearing surfaces, etc.

Figure 1:
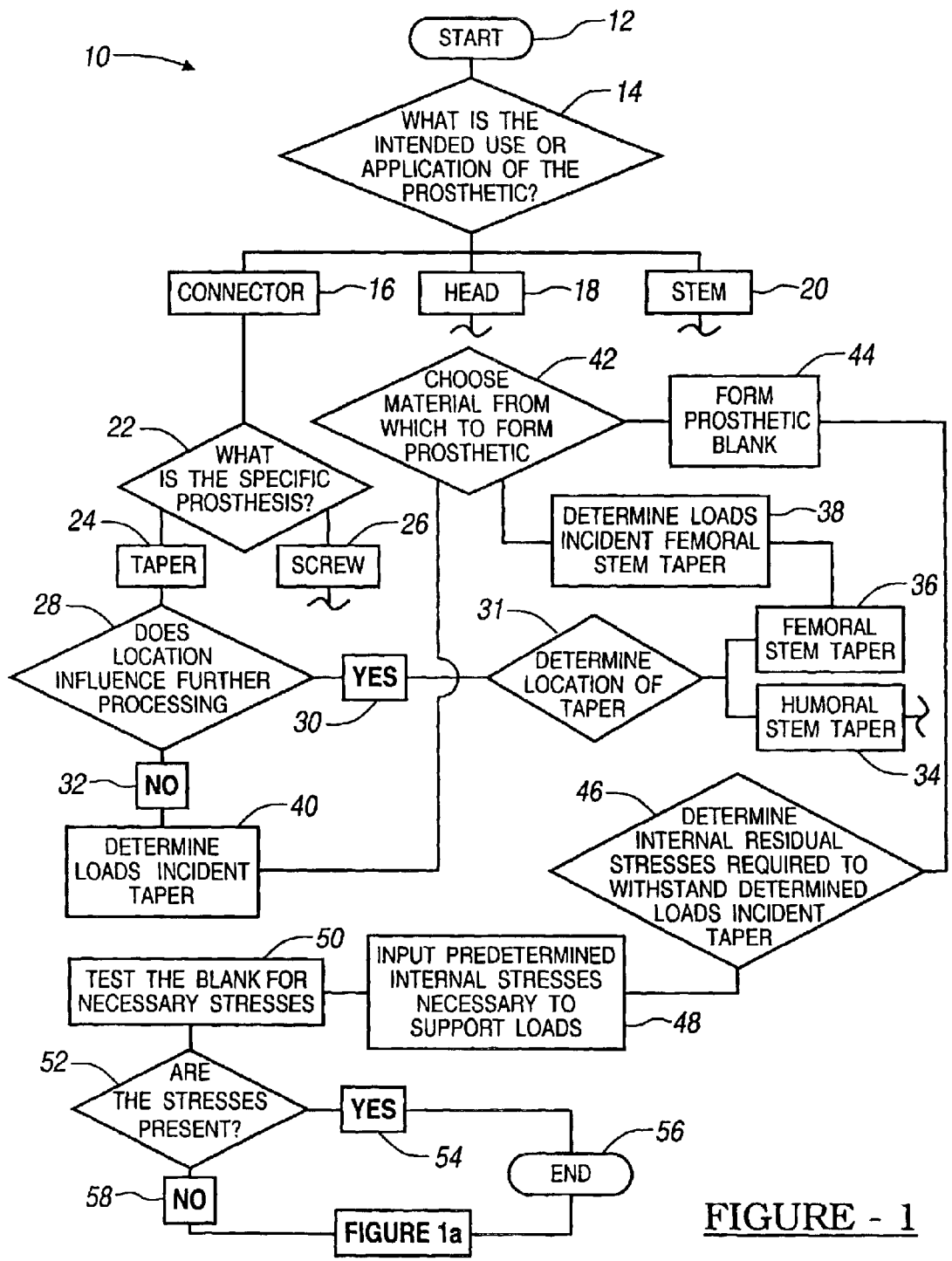
FIG. 1 is a flow chart regarding the method of producing a prosthetic implant according to a first embodiment of the present invention.

With reference to FIG. 1, a prosthesis device production process 10 is illustrated in a flow chart. The process 10 may be used to produce any number of prosthetic devices for implantation. It will be understood, however, that the produced prosthetic devices may be implanted into any body which requires a prosthesis. The process 10 begins at a start block 12. Then a determination of a group or class prosthetic device to be produced occurs in decision block 14. General groups or classes of prosthetic devices include a connector 16, a head 18, or a stem 20. It will be understood that the process 10 can be used to produce any prosthetic device for implantation.

After choosing a connector in block 16, a specific connector to be produced must be determined in a decision block 22. Particular connectors may include tapers 24 or screws 26. Although the description herein will follow the production of a male taper or a Morse taper, the process may be substantially the same for any prosthetic device which is to be produced. It will also be understood that the connector described herein may be used in conjunction with many prosthetic devices. For example, a Morse taper connector may extend from a modular head or a modular stem to form a Morse taper connection with another portion, such as a Morse taper connection between a modular stem and a modular head. Another exemplary use of a Morse taper is to connect modular portions of a stem implanted into bone. Other connectors may connect a prosthetic device to a portion of the human anatomy. For example, a screw may be used to interconnect the prosthesis and a bone.

Once the taper 24 is chosen, it must be determined, in determination block 28, whether the location of the taper imparts particular loads which the taper will be subjected. Again, as described further herein, this determination is important and determines what cold working or work hardening needs be done to the taper to impart in the taper a particular physical characteristic, such as residual stress. Essentially, determining whether the location of the taper produces any unique loads which the taper will need to withstand is an intermediate step to determining the loads which will be incident the taper. The determination block 28 can have two particular outcomes a Yes block 30 or a No block 32. If it is determined, in the determination block 28, that the Yes block 30 must be preceded, then the particular location of the taper is determined. The location of the taper may be any general location such as a humeral stem block 34 or a femoral stem block 36. It will be understood, however, that the taper may be determined to be in any location for implantation. If the femoral stem taper is chosen in block 36, then it must be determined in the loads incident the femoral stem taper after implantation in determination block 38. Here the loads that may be incident the femoral stem chosen in block 36 can be determined.

Even if the particular location of the taper is not relevant to determining the loads incident to the taper, and No block 32 is chosen, the loads incident the taper are determined in determination block 40. If the particular location of the taper is not particularly relevant, it may simply be that the loads incident the taper relate to a preferred or required strength that the taper must withstand. Therefore, determining the loads incident the taper may simply be creating a taper that is within known or required strength limits. Generally, and especially if location is relevant to loads to be experienced by the taper, loads incident to the taper will be determined through laboratory testing of the natural joint in a test subject. In other cases, the loads incident taper may be known through previously conducted studies or reference materials. In any case, the load incident taper is determined in block 38 or 40.

After determining the loads incident the taper block 38 or 40, determining the material from which the taper will be formed follows in determination block 42. Generally, materials for use in prosthetic devices are biocompatible and have substantial innate strength and longevity. Materials commonly used for forming prosthetics, for many uses in the body, include Titanium, Titanium alloys, and other metal alloys, such as cobalt alloys and stainless steel. It will also be understood that other materials, such as high molecular weight polyethylene, may also be used to form prosthetic devices for use in implantation. These other materials may augment the metallic portions of the prosthetic implant.

A blank prosthetic taper, also known as uncold-worked or unwork-hardened, is then formed in block 44. The blank prosthetic taper is formed to substantially include all of the external dimensions required of the final prosthetic taper, save for any work hardening procedures that occur to create the final prosthetic taper. Therefore, it is understood that the blank prosthetic taper is the prosthetic taper that is formed from the material chosen to form the prosthetic while being unworked. The blank prosthetic may be formed using any appropriate technique including forging or casting.

After the forming of the blank prosthetic block 44, it can be determined, in determination block 46, the residual stresses required in the prosthetic to withstand the loads determined in determination blocks 38 or 40. In particular, the determined loads incident the taper must be withstood for a particular period of time after implantation of the taper. Particular residual stresses which may be present or produced in the taper, increase the longevity or increase the desirability of a particular taper over another. Therefore, it is determined the desired or required internal residual stresses which are to be present in the taper.

Here, in determination block 46, particular internal residual stresses, which may increase the longevity of the connector, are determined. They may be determined through any known means such as creating test prosthetics and testing them for wear or failure rates. Then the precise internal stresses along with their location in the prosthetic and type are measured and predetermined for the most desirable prosthetics. Therefore many, if not all, of the internal stresses which are most desirable in a connector to produce one with the greatest longevity and wear resistance are predetermined for further input into the system 10.

After determining the preferred residual stresses in block 46 the predetermined residual stresses are input in block 48 into the process 10. This may simply be that the predetermined internal stresses are input into a testing device to determine whether the blank prosthetic includes these internal stresses. Otherwise, inputting the predetermined internal stresses may be an inherent portion of the process 10 to ensure that the process 10 creates the proper internal stresses in the prosthetic taper. In any case, inputting the predetermined internal stresses ensures that the final product includes the internal stresses to withstand the loads incident the taper.

These internal stresses are generally measured in the units of ksi, MPa, or percent cold worked. Therefore, not only the pressures present in the material, but the amount of cold working present also may be used and will be understood to represent the internal stresses. The internal residual stresses help determine the amount of compression and extension, and the amount of lateral and medial movement the male taper may undergo before failing. The particular internal stresses to be produced may also decrease surface defects which may form after implantation such as cavitations and cracks. All of these increase the longevity of the prosthetic taper. In addition, the internal stresses that are produced through the process 10 can increase the strength of the prosthetic taper. In any case, the predetermined internal residual stresses, which are input into the process 10, are consistently produced in the prosthetic which is formed using the process 10. Thus, producing prosthetics which may include random amounts of residual stresses, which may or may not produce a prosthetic that has the most desirable qualities, is reduced. Using the process 10 where the predetermined internal stresses are input block 48, the prosthetic will always include the particular internal residual stresses which are most desirable in that prosthetic.

After the predetermined internal stresses are input into the process 10, the blank prosthetic taper formed in block 44 is tested for these predetermined internal stresses in block 50. The blank prosthetic taper can be tested using any known end appropriate technique to determine whether particular internal residual stresses are present. One known method includes X-ray crystal diffraction to determine the type and amount of residual stresses and cold working present. It can also be determined whether the residual stresses of a particular nature and amounts are present at different depths within the blank taper. The testing performed in block 50 may also be used as quality control or quality assurance measures.

After testing the blank prosthetic, it can be determined whether the predetermined residual stresses are present in block 52. If Yes block 54 is determined then the internal stresses are present in the blank taper, which match the input predetermined internal stresses, then the prosthetic taper has been formed and the process ends at block 56. Simply, if the predetermined internal stresses are present in the blank prosthetic taper, then additional cold working or work hardening is not required. The internal stresses are already present in a magnitude great enough to hold the load which will be incident the taper, then the taper is considered finished and the process ends.

Figure 1A:
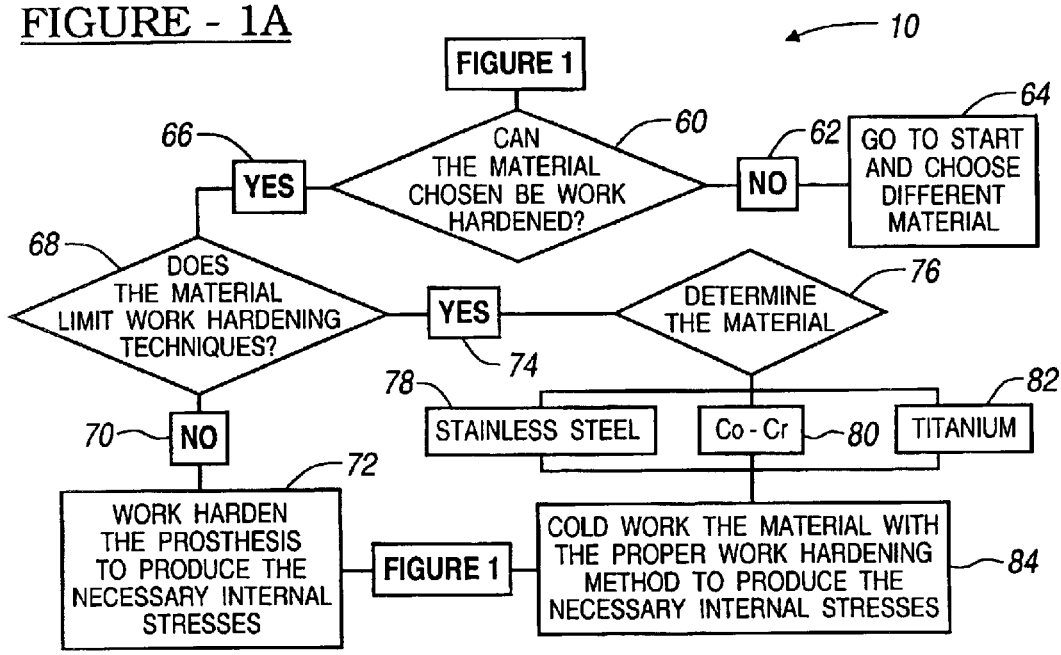

If the No block 58 is determined, then cold working must be performed to instill or produce in the Morse taper the predetermined internal stresses. Turning reference to FIG. 1*a*, first it is determined, in block 60, if the material chosen in block 42 can be work hardened. If it Is determined that the material or the prosthetic formed cannot be work hardened, in the block 62, to induce the required internal stresses then the blank prosthetic is not useable for the determined use. If such an instance occurs, then the process mustre-start in block 64 and a different material must be chosen in block 42.

If Yes is chosen in block 66, then the material can be work hardened and a determination of whether the material chosen will require any particular or unique work hardening processes must be determined in determination block 68. As described herein, the blank prosthesis is cold worked to impart the predetermined internal stresses. If it is determined that the material does not require any particular, unique, or different processing, in block 70 then the blank prosthetic is work hardened in process block 72.

Cold working or work hardening is performed on the Morse taper, in process block 72, to produce the predetermined internal stresses necessary to hold the loads which will be incident the taper. Any appropriate cold working method may be used to create the internal stresses to withstand the loads incident the taper. One such method is described in the commonly assigned U.S. Pat. No. 6,067,701 to Mark B. Vandewalle entitled "Method for Forming a Work Hardened Modular Component Connector" which is hereby incorporated by reference. It will be understood, however, that a plurality of other methods may be used to work harden the male taper. Other methods include, for example, shot peening or laser shock peening the taper. None of these methods alone, however, predetermine the amount of desired work hardening necessary, as is set forth in the present invention. After work hardening in block 72, then the end block 56 is reached and the Morse taper is complete.

If the material limits the work hardening techniques as determined in determination block 68, then Yes block 74 is chosen. Then a determination of the particular material is made in the determination block 76. Exemplary determined materials include stainless steel 78, cobalt chromium alloys 80, and titanium alloys 82. It will be understood, however, that other appropriate materials may be determined in determination block 76. Simply any appropriate material may be chosen in block 42 from which to form the prosthesis in the process 10. After the material is determined, then the blank prosthetic is cold worked in the process block 84 using the appropriate unique cold working or work hardening method to produce the predetermined internal stresses in the blank taper. After the predetermined internal stresses are produced in the blank taper, then the process 10 proceeds to the end block 56. After this, a finished or work hardened prosthetic taper is formed.

Moving back up the process 10, if it is determined Yes in block 30 that the location of the taper is relevant, then the location of the taper is determined in block 31. The taper may be in any one of numerous locations, such as a humeral stem 34 or a femoral stem 36. It will be understood that, though the process of forming a femoral stem is described further herein, that no matter the location of the taper, the process would be substantially similar to the method described above.

Generally, the femoral stem taper in a modular hip prosthesis has residual stresses predetermined between about a range of 40 ksi to at least about 120 ksi at a depth to at least about 3 mm below the exterior surface of the taper. It will be understood that the internal stresses may be present at any depth between the exterior surface and at least about 3 mm below the exterior surface. As discussed above, if these stresses are present, then the process ends and the femoral stem taper has the necessary internal stresses to hold the loads that are incident the taper on the femoral stem. If it is determined, however, that the predetermined internal stresses are not present which are necessary to withstand the loads incident the femoral stem, then cold working or work hardening is used to produce the internal stresses.

Again, as discussed above, any one of a number of appropriate methods may be used to cold work or work harden the male taper on the femoral stem to produce the predetermined internal stresses. Regardless of the work hardening method used to work harden the male taper, the internal stresses produced in the taper are those that have been predetermined. Therefore, it is these predetermined internal stresses which are formed in the taper using the preferred work hardening method. Therefore, the process of work hardening the taper is not exploratory, but rather known. That is, the internal stresses are either present in determination block 52 or produced in the blank prosthetic taper in later work hardening, process blocks 72 or 84 regardless they are predetermined in determination block 46. Rather than simply cold working a blank prosthetic to produce an unknown internal residual stresses, the residual stresses are determined as a block in the process 10. Therefore, the internal residual stresses are known and unmistakably produced to form the final prosthetic.

The internal stresses in the blank prosthetic formed in block 44 may be determined using any appropriate means, for example X-ray crystal di-fraction (X-ray diffraction) in accordance with SAE J784 and ASTM E1476 and other known standards. These tests are used to determine the amount of diffraction of the X-rays through the materials, particularly the grains and spacing between the grains are determined using these tests. The percent cold working can then be determined or inferred looking at the breadth of the diffraction peaks at half height. From these tests, the internal stresses or percent cold working can be determined as general absolutes and then formed in other prosthetic devices without resorting to fatigue testing of the prosthetic devices after forming them with these predetermined residual stresses. This testing process can determine the internal stresses and percent cold working at a number of different depths in the taper. The test determines whether the predetermined internal stresses are present at varying depths. These internal stresses are predetermined and may be dependent upon the particular use or application of the prosthesis. It will be understood, however, that one set of particular internal stresses may be used for any number of appropriate or particular uses.

Testing of particular work hardened prosthesis using techniques, such as X-ray diffraction, can be used to optimize the process 10. Several work hardened prosthetics may be formed which are then tested by X-ray diffraction to determine the produced internal stresses. The work hardened male tapers may be tested to determine which method or which internal stresses produce the strongest and longest lasting prosthetic. Therefore, the predetermined internal stresses can be refined to produce the best or most preferred internal stresses for the different prosthetics. This determination, along with the known loads incident that prosthetic, are used to form the predetermined internal stresses. Again, the internal stresses are predetermined before prosthetics formed for use in implantation procedures are produced.

Figure 2:
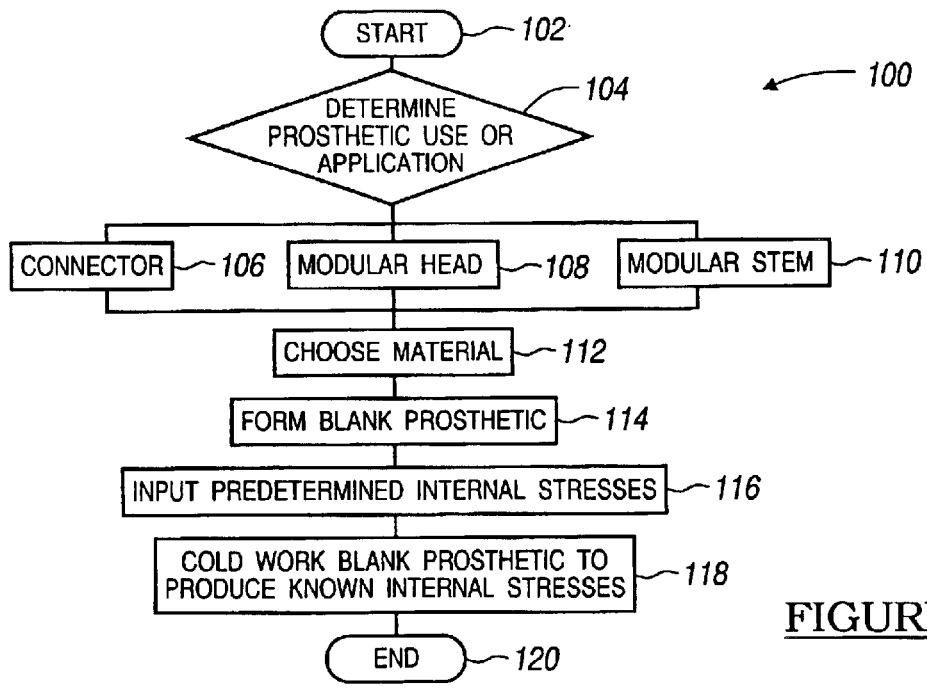
FIG. 2 is a flow chart of a method to produce a work hardened prosthetic implant according to a second embodiment of the present invention.

It will also be understood that a production process for forming a blank prosthetic taper, that is the blank prosthetic formed in block 44, generally produces a taper having particular internal stresses and properties These blank prosthetics generally all require a particular range of cold working to form the predetermined internal stresses. Therefore, it will be understood that particular process blocks, such as the testing block 52 and other determination blocks may be skipped, thus producing a blank taper which is then cold worked or work hardened in a similar or standard manner. A second embodiment of the present invention, illustrated in FIG. 2, includes a process 100 including fewer blocks than process 10 to produce a taper with predetermined internal stresses. When it is known that substantially all prosthetics are to be work harden at a substantially similar amount the process 100 may be employed.

The process 100 is substantially shortened over the first embodiment process 10. After starting in block 102, the application or use of the prosthetic to be formed is determined in block 104. Prosthetics chosen in block 104 may include any prosthetic such as a connector 106, modular head 108, or modular stem 110. After the particular use of the prosthetic is determined, a material from which the prosthesis is formed is chosen in block 112. It is understood that any appropriate material may be chosen such as titanium or cobalt chromium alloys. Then, a blank prosthetic is formed, in block 114, from the chosen material. Choosing the material in block 112 may also be melded into determining which prosthetic to be produced, in block 104, such that each particular prosthetic will only be formed from one particular material.

Therefore, after the blank prosthetic is formed, the predetermined internal stresses, for that particular prosthetic, are input in block 116. Simply the internal stresses which have been predetermined for the particular prosthetic are input into the process 100. The stresses are known and may be saved in a computer readable table or an engineer input table. The stresses may then be input into the system 100 with a computer reading the table or by a human engineer. The table includes the known and predetermined information for particular stresses required for various applications and materials. Then, the blank prosthetic is cold worked to produce the predetermined internal stresses in process block 118. This forms a work hardened prosthetic including the predetermined internal stresses and the end 120 is reached.

Figure 3:
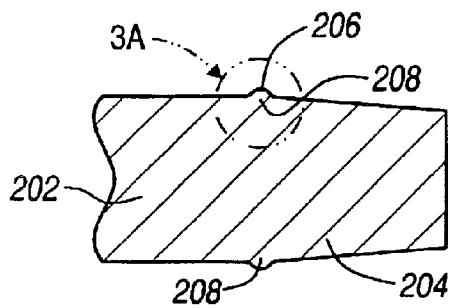
FIG. 3 is a cross sectional view of a blank Morse taper according to a first embodiment of the present invention.
Figure 3A:
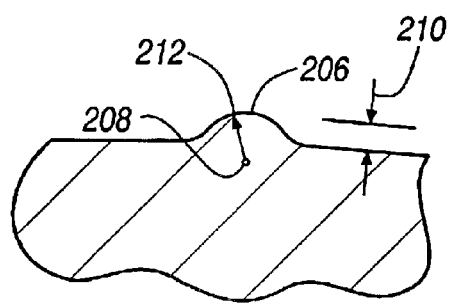
FIG. 3a is a detailed view of circle 3a from FIG. 3.
Figure 4:
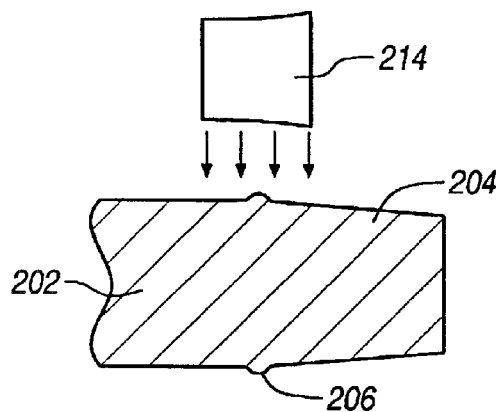
FIG. 4 is a schematic of roller hardening a taper.
Figure 5:
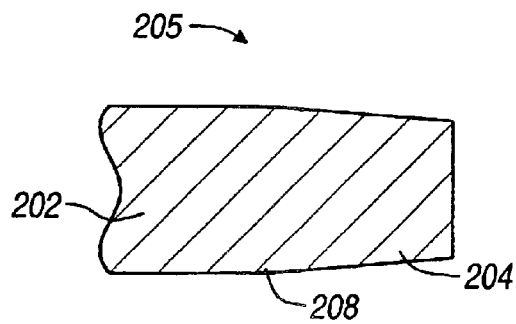
FIG. 5 illustrates a work hardened prosthesis produced according to the present invention.

With reference to FIGS. 3–5, an exemplary embodiment of cold working a male taper according to the process 10 is illustrated. The process is initially started at block 12. After which, the intended use of the prosthetic is determined. In relation to FIG. 3–5 a connector, such as shown in block 16, will be produced. The specific prosthetic, as chosen in block 22, is a taper as shown in block 24. Next a determination of whether the location influences further processing, as determined in block 26, is made. Here it is determined that Yes, as in block 30, is the most prudent choice. Therefore, the location of the taper is determined, in block 31. The taper illustrated in FIGS. 3–5 is specifically for a femoral stem taper, as chosen in block 36. The femoral steam taper is a mid-body junction. In a mid-body junction, the taper is used to connect two modular portions of a femoral stem implant within a bone. The femoral stem taper may also be the taper which extends from a stem which is implanted into the femur for a modular hip implant onto which a head would be placed. After determining the location of the femoral male taper, the loads incident the femoral male taper are determined, as in block 38. The loads generally incident a male taper in a femoral implant are between about 100 kg to at least about 1600 kg. When a tailored or custom taper is formed loads determined to be incident, the male taper are generally at least about twice the patient's body mass.

Once the loads are determined, the material from which the prosthetic is formed is chosen, as in block 42. Generally, femoral tapers are formed from a biocompatible metal such as Titanium alloy. After choosing the material, a blank prosthesis is formed as in block 44. Once the blank prosthetic is formed, a determination of the internal residual stresses required or most desired to withstand the determined loads incident the femoral taper, as shown in block 46, is made. The internal residual compressive stresses for a femoral stem male taper are about 40 ksi to about 120 ksi and present at up to 3 mm below the surface of the taper.

After the desired internal residual stresses are determined, they are input into the process, as in block 48. Once the predetermined residual stresses are input into the process, the blank prosthetic may be tested for these internal stresses, as in block 50. It is determined whether the stresses are present in the blank prosthetic, as in block 52. If No is chosen, as in block 58, then it must be determined whether the material which was chosen to form the femoral male taper can be work hardened, such as in block 60.

If Yes is chosen, as in block 66, it is determined whether the material from which the male taper is formed requires unique work hardening techniques, such as determined in block 68. If Yes is chosen, such as in block 74, the particular material is determined or recalled such as in block 76. In this example, Titanium alloy, such as that in block 80, is being used. After the material is determined, the particular work hardening techniques are carried out, as in block 84. The following discussion describes a particular cold working technique which uses roller hardening to produce the desired internal stresses in the male taper.

A cylindrical stock portion of material, such as Titanium alloy, is lathed. The stock piece may be lathed on any particular lathe such as a precision CNC lathe. Once positioned in the lathe, a first cylindrical portion 202 and a second cylindrical taper portion 204 to form a taper member 205 is produced from the stock piece. Generally, this can be produced by rotating the stock and lathing off a portion to produce the taper member 205.

The tapered portion 204 is turned to a slightly oversized diameter along the entire length of the tapered portion 204. In addition, a toroidal bump or raised ridge 206 is formed at a transition corner 208 between the first cylindrical portion 202 and the tapered portion 204. This produces a raised ridge 206 that is higher than the taper portion 204 as indicated at reference 210 and has a radius as identified at reference numeral 212. A cylindrical portion 202, the raised ridge 206, and the tapered portion 204 can all be formed at the same time on the lathe. Therefore, each portion is substantially concentric.

With particular reference to FIG. 4, the raised ridge 206 can be compressed into the transition region 208 using a roller 214. Any appropriate roller 214 may be used as long as it has enough rigidity to force the raised ridge 206 into the transition region 208. Therefore, two portions 202 and 204 are rotated, the roller 214 is forced onto the surface. This forces the raised ridge 206 into the transition region 208 and reduces the height of the raised ridge 206 such that it is substantially flat with the surrounding areas. The roller may produce irregularities as it is cold working the surface which may be removed using the CNC lathe in an appropriate final machining.

This example compressed the raised ridge 206 into transition region 208, such that the surface of the male taper is substantially even. Final machining then smoothes the surface further. In addition roller hardening, according to this example can compress an entire oversized surface of the taper portion 204. This example may produce residual compressive stresses in a range between about 40 ksi to about 100 ksi in the taper portion 204 and at the transition corner 208. These compressive forces are formed in a region of the surface between the exterior and at least about 3 mm below the exterior surface.

The final machining, however, does not reduce the work hardening effect or remove the work hardening stresses produced in the above described processes. In addition, a work hardened taper 220 hardened through the work hardening of the described process 10, 100 generally has a cantilever beam fatigue strength that is about 1.5 times to at least about 3 times stronger than an unwork hardened taper of the same material and having similar finished dimensions. This may translate to a male taper which does not need to be replaced for many times the loading cycle of a taper that is not work hardened. Alternatively, a smaller taper can be used in the same application. It will be understood, however, that the above described method is merely exemplary and any appropriate method may work harden a prosthetic to produce the predetermined internal stresses, such as shot peening or laser shock peening.

It will also be understood that various methods of cold working may require various lengths or intensities of cold working. For instance, cold rolling, as discussed above, may require the compression of a bump or a raised ridge or portion on the male taper a certain amount, as previously described. Other cold working methods, such as shot peening, may require the subjection of the male taper to a particular density of shot for a particular amount of time. It will be understood, however, that regardless of the method chosen, producing the predetermined internal stress is the ultimate result to withstand the loads incident the particular male taper. Also different materials may require different types or lengths of cold working as well.

The above disclosure is merely exemplary of the present invention. As mentioned above, the methods described herein may be used to produce other prosthetic devices, such as a modular head or a modular stem, which require particular internal physical characteristics to withstand the loads incident the prosthetic after implantation. Again, once the steps are determined and particular internal characteristics, such as internal stresses, are known for the prosthetic device, cold working may be performed on any of the prosthetic devices to produce the predetermined internal stress.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method of forming a prosthetic device comprising:
   determining a use for a prosthetic device;
   determining loads said prosthetic device will encounter in said use;
   choosing a material to form a blank prosthetic device having an initial bearing capacity for said loads;
   determining an internal stress of said prosthetic device to withstand said loads; and
   forming said prosthetic device to include said predetermined internal stress, wherein the determined internal stress for the prosthetic device is about 40 ksi to about 120 ksi.

2. The method of claim 1, wherein said prosthetic device comprises a connector.

3. The method of claim 2, wherein said connector is a male taper to form a Morse taper with a female taper in a modular femoral head.

4. The method of claim 3, wherein said step of determining said internal stress comprises:
   work hardening said taper; and
   performing X-ray crystal diffraction on said work hardened taper to determine internal stress.

5. The method of claim 1, wherein said step of forming said prosthetic device comprises:
   forming a blank male taper; and
   shot peening said male taper to create in said male taper said determined internal stress.

6. The method of claim 1, wherein said step of forming said prosthetic device comprises:
   forming a blank male taper; and
   cold working said blank taper by compressing said blank male taper to instill said determined internal stress.

7. The method of claim 1, further comprising forming the prosthetic device as an acetabular cup, a femoral head, a humeral connection taper, a femoral connection taper, a stem, or combinations thereof.

8. The method of claim 7, wherein the acetabular cup is formed to have a bearing surface, wherein the determined internal stress is formed at a depth below the bearing surface.

9. The method of claim 7, further comprising:
   forming a prosthetic device as a male taper;
   work hardening the male taper to form the determined internal stresses at a selected depth below the exterior surface of the male taper.

10. The method of claim 1, wherein forming said prosthetic device to include said predetermined internal stress includes forming an internal residual compressive stress, an internal residual tensile stress, or combinations thereof.

11. A method of forming a prosthetic device comprising:
    determining the prosthetic device to include a male taper;
    determining a use for a prosthetic device;
    determining loads said prosthetic device will encounter in said use;
    choosing a material to form a blank prosthetic device having an initial bearing capacity for said loads;
    determining an internal stress of said prosthetic device to withstand said loads; and
    forming said prosthetic device to include said predetermined internal stress,
    wherein said predetermined internal stress for said femoral male taper is about 40 ksi to about 120 ksi in a region between an exterior surface of said male taper and at least about 3 mm below the exterior surface.

12. The method of claim 11, wherein forming said prosthetic device to include said predetermined internal stress includes forming an internal residual compressive stress, an internal residual tensile stress, or combinations thereof.

13. A method of forming a prosthetic device comprising:
    determining a use for a prosthetic device;
    determining loads said prosthetic device will encounter in said use;
    determining an internal stress of said prosthetic device to withstand said loads; and
    forming said prosthetic device to include said predetermined internal stress;
    wherein said step of forming said prosthetic device comprises:
    forming a blank male taper; and
    laser shock peening said blank male taper to create in said blank male taper said determined internal stress.

14. A method for producing a prosthetic device for implantation into a body comprising:
    determining an application for said prosthetic device;
    forming said prosthetic device for said application;
    determining loads incident said prosthetic device when applied to said application;
    determining a particular internal stress required in said prosthetic device when in said application; and
    producing said predetermined particular internal stress in said prosthetic device, wherein the determined internal stress for the prosthetic device is about 40 ksi to about 120 ksi at a selected depth in a region between an exterior surface of the prosthetic device and at least about 3 mm below the exterior surface.

15. The method of claim 14, wherein forming said prosthetic device comprises:
    forming a blank prosthesis comprising a male taper extending from said blank prosthesis;
    machining said male taper; and
    cold working said male taper to produce said particular internal stresses in said male taper.

16. The method of claim 15, further comprising rolling said male taper such that said male taper is compressed.

17. The method of claim 15, wherein cold working said male taper comprises impinging projectiles on said male taper.

18. The method of claim 15, wherein forming said prosthetic device comprises:
   casting a modular implant adapted to interconnect a bone portion and a modular component comprising a male taper;
   machining said male taper to interconnect with a female taper; and
   forming a modular component defining said female taper.

19. The method of claim 14, wherein forming said prosthetic device to include said predetermined internal stress includes forming an internal residual compressive stress, an internal residual tensile stress, or combinations thereof.

20. A method for producing a prosthetic device for implantation into a body comprising:
   determining an application for said prosthetic device;
   forming said prosthetic device for said application;
   determining loads incident said prosthetic device when applied to said application;
   determining a particular internal stress required in said prosthetic device when in said application; and
   producing said predetermined particular internal stress in said prosthetic device;
   wherein forming said prosthetic device comprises:
   forming a blank prosthesis comprising a male taper extending from said blank prosthesis;
   machining said male taper; and
   cold working said male taper to produce said particular internal stresses in said male taper;
   wherein said male taper extends from a femoral stem; and
   wherein cold working said male taper to produce said predetermined particular internal stresses includes producing about 40 ksi to about 120 ksi in a region between an exterior surface of said femoral male taper and at least about 3 mm below the exterior surface.

21. The method of claim 20, wherein cold working said male taper to produce said determined particular internal stresses includes forming an internal residual compressive stress, an internal residual tensile stress, or combinations thereof.

22. A method for producing a prosthetic device for implantation into a body comprising:
   determining an application for said prosthetic device;
   forming said prosthetic device for said application;
   determining loads incident said prosthetic device when applied to said application;
   determining a particular internal stress required in said prosthetic device when in said application; and
   producing said predetermined particular internal stress in said prosthetic device;
   wherein forming said prosthetic device comprises:
   forming a blank prosthesis comprising a male taper extending from said blank prosthesis;
   machining said male taper; and
   cold working said male taper to produce said particular internal stresses in said male taper;
   wherein cold working said male taper comprises laser shock peening said male taper.

23. A method for producing a prosthetic device for implantation into a body comprising:
   determining an application for said prosthetic device;
   forming said prosthetic device for said application;
   determining loads incident said prosthetic device when applied to said application;
   determining a particular internal stress required in said prosthetic device when in said application; and
   producing said predetermined particular internal stress in said prosthetic device,
   wherein determining said particular internal stress comprises:
   forming a plurality of test prostheses comprising varying internal stresses;
   determining which of said plurality of test prostheses carries said load; and
   determining an internal stress of said test prosthesis which carries said load.

24. A method of producing a prosthetic for implantation comprising a particular internal stress, the method comprising:
   determining a use for a prosthetic member;
   forming a blank comprising a body and a connector;
   determining loads that said connector will encounter after implantation;
   testing said blank for carrying said determined loads;
   determining particular internal stresses generally necessary to carry said determined loads; and
   cold working said connector to produce said particular internal stresses in said connector of said blank to form said prosthetic member.

25. The method of claim 24,
   wherein said use for said prosthetic member is a femoral prosthesis; and
   wherein said body comprises a modular stem and said connector comprises a male taper of a Morse taper.

26. The method of claim 25, wherein determining the loads comprises determining the loads said femoral prosthesis will encounter once implanted into a femur.

27. The method of claim 25, wherein said determined internal stresses are about 40 ksi and to at least about 120 ksi.

28. The method of claim 27, wherein said determined internal stresses include an internal residual compressive stress, an internal residual tensile stress, or combinations thereof.

29. The method of claim 25, wherein cold working comprises cold rolling said male taper to substantially compress said male taper.

30. The method of claim 24, wherein determining a use for said prosthetic member comprises designing said connector comprising a mate taper.

31. The method of claim 24, wherein cold working said connector includes impinging projectiles on said connector.

32. The method of claim 24, wherein cold working said connector comprises laser shock peening said connector.

33. A method of producing a prosthetic member for implantation comprising a predetermined particular internal stress, the method comprising:
   determining a use for a finished prosthetic member;
   forming a blank prosthetic member comprising a femoral male taper;
   determining a particular residual internal stress of about 40 ksi to at least about 120 ksi to be formed in a region between an exterior surface of said femoral male taper and at least about 3 mm below the exterior surface; and work hardening said blank prosthetic member to produce said predetermined internal stresses in said blank prosthetic to form said finished prosthetic member.

34. The method of claim 33, wherein forming said blank prosthetic member includes forming a stock member of a metal alloy selected from a group consisting of chromium alloys, Titanium alloys, or combinations of both into a blank femoral male taper.

35. The method of claim 33, wherein work hardening said femoral male taper includes compressing substantially an entire exterior of said blank prosthetic.

36. The method of claim 33, wherein work hardening said blank prosthetic member to produce said predetermined internal stresses includes forming an internal residual compressive stress, an internal residual tensile stress, or combinations thereof.

* * * * *

(12) EX PARTE REEXAMINATION CERTIFICATE (7065th)
United States Patent
Gibbs et al.

(10) Number: US 6,911,100 C1
(45) Certificate Issued: Sep. 15, 2009

(54) METHOD FOR CONTROLLING RESIDUAL STRESS IN PROSTHETICS

(75) Inventors: Phillip Martin Gibbs, Winona Lake, IN (US); Dave Wayne Schroeder, Winona Lake, IN (US)

(73) Assignee: Biomet, Inc., Warsaw, IN (US)

Reexamination Request:
No. 90/008,627, Jun. 15, 2007

Reexamination Certificate for:
Patent No.: 6,911,100
Issued: Jun. 28, 2005
Appl. No.: 10/231,944
Filed: Aug. 30, 2002

(51) Int. Cl.
*A61F 2/30* (2006.01)
*A61F 2/36* (2006.01)

(52) U.S. Cl. ............ 148/668; 148/670; 29/407.05; 623/20.35; 623/20.36; 623/23.11
(58) Field of Classification Search .............. None
See application file for complete search history.

(56) References Cited

U.S. PATENT DOCUMENTS

| 3,357,458 A | 12/1967 | Radd et al. |
| 5,704,239 A | 1/1998 | Beals et al. |
| 6,067,701 A | 5/2000 | Vandewalle |
| 6,474,135 B1 * | 11/2002 | Clauer et al. ............... 73/12.01 |

FOREIGN PATENT DOCUMENTS

CA 2282035 A1 3/2000

OTHER PUBLICATIONS

Dowling, Norman, E., "Mechanical Behavior of Materials," 1999, pp. 1–20, Prentice–Hall, Inc., USA.
Long, Marc et al., "Titanium alloys in total joint replacement–a materials science perspective," Biomaterials, 1998, pp. 1621–1639, vol. 19, Elsevier Science, Ltd., USA.
Wagner, L. et al., "Influence of Surface Condition on Fatigue Strength," Fatigue 90, 1990, pp. 323–328, vol. 1, Materials and Component Engineering Publications Ltd., UK.

* cited by examiner

*Primary Examiner*—Krisanne Jastrzab

(57) ABSTRACT

A method for producing predetermined internal stresses in a prosthetic device for implantation. The method includes first determining internal stresses which are preferred in prosthetics to instill a particular strength and longevity to the prosthetic. In particular, internal stresses may be used to increase the strength of smaller prosthetic devices. Additionally, once the preferred internal stresses are determined, the internal stresses can be cold worked into subsequent prosthetic devices to instill the same characteristics. Once parts are manufactured, internal stresses can be measured to validate manufacturing process and serve as verification for quality control purposes. Producing prosthetic devices, including predetermined internal stresses through work hardening the prosthetic devices, is described.

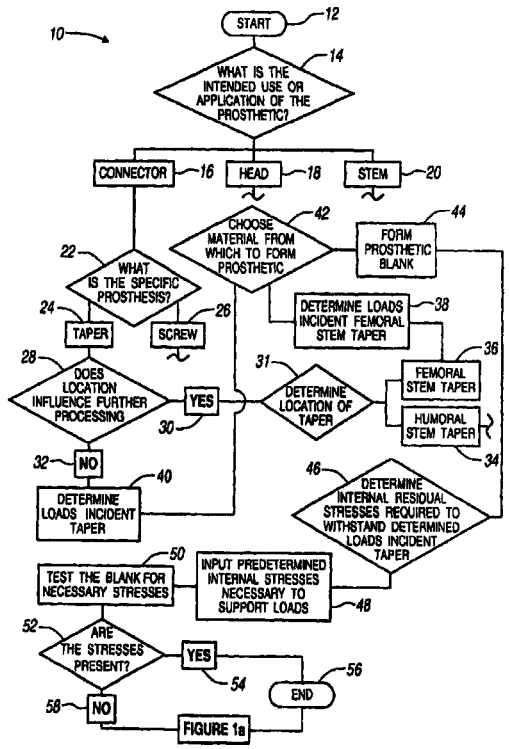

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–36 are cancelled.

* * * * *